US00PP32384P2

(12) United States Plant Patent
Heuger

(10) Patent No.: US PP32,384 P2
(45) Date of Patent: Oct. 20, 2020

(54) ***HELLEBORUS* PLANT NAMED 'COSEH 5400'**

(50) Latin Name: ***Helleborus* x *ericsmithii* X *Helleborus* x *hybridus***
Varietal Denomination: COSEH 5400

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 16/602,792

(22) Filed: Nov. 29, 2019

(51) Int. Cl.
*A01H 5/02* (2018.01)
*A01H 6/72* (2018.01)

(52) U.S. Cl.
USPC ..... Plt./439

(58) Field of Classification Search
USPC ..... Plt./263.1, 439
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Helleborus* plant named 'COSEH 5400', characterized by its upright and mounded plant habit; moderately vigorous to vigorous growth habit; dark green-colored leaves; freely flowering habit; single white and red purple bi-colored flowers; and good garden performance.

2 Drawing Sheets

Figure 1:
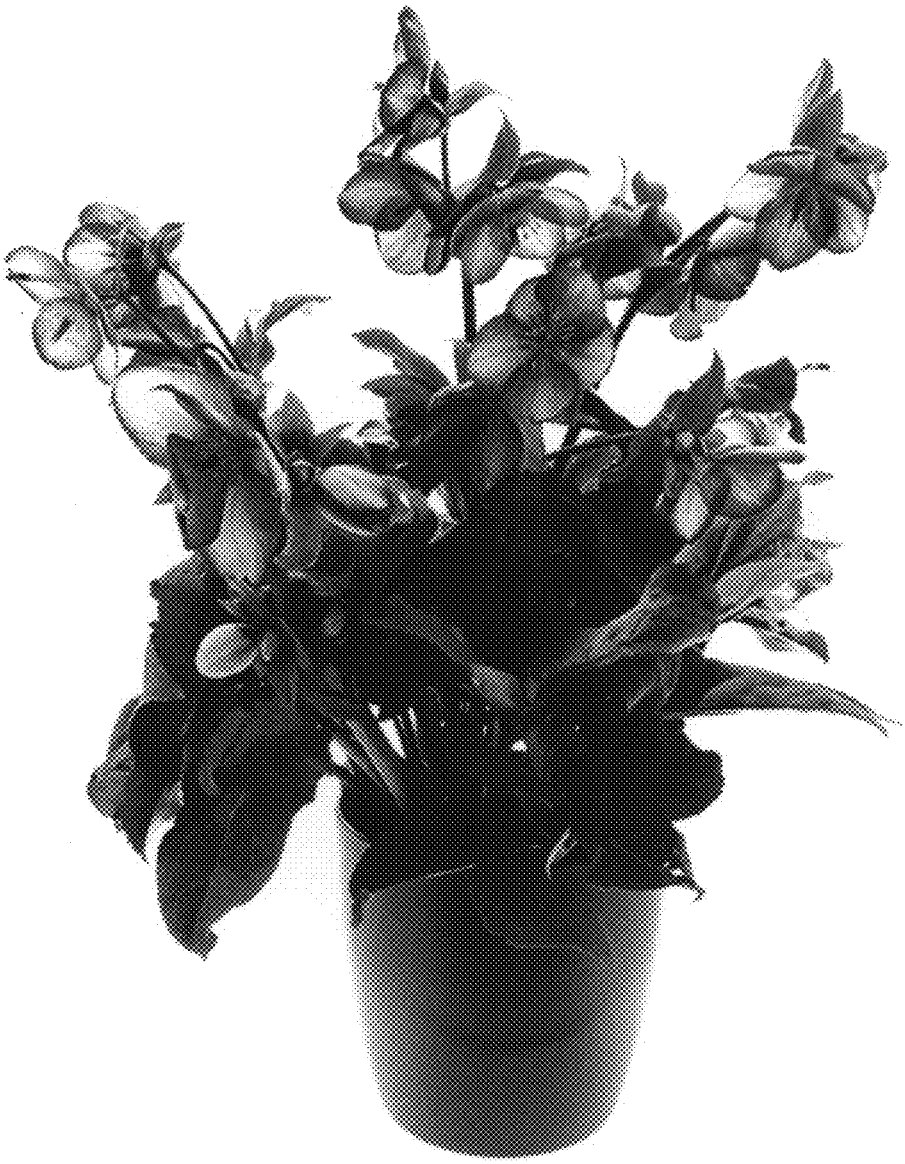

Botanical designation: *Helleborus* x *ericsmithii* X *Helleborus* x *hybridus*.
Cultivar denomination: 'COSEH 5400'.

CROSS-REFERENCED TO CLOSELY-RELATED APPLICATIONS

Title: *Helleborus* Plant Named 'COSEH 5100'
Applicant: Josef Heuger
Filed: Concurrently with the instant application U.S. Plant patent application Ser. No. 16/602,772
Title: *Helleborus* Plant Named 'COSEH 5200'
Applicant: Josef Heuger
Filed: Concurrently with the instant application U.S. Plant patent application Ser. No. 16/602,786
Title: *Helleborus* Plant Named 'COSEH 5300'
Applicant: Josef Heuger
Filed: Concurrently with the instant application U.S. Plant patent application Ser. No. 16/602,773

BACKGROUND OF THE INVENTION

The present invention relates to a new and distinct cultivar of *Helleborus* plant, botanically known as *Helleborus* x *ericsmithii* X *Helleborus* x *hybridus* and hereinafter referred to by the name 'COSEH 5400'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stress.

The new *Helleborus* plant originated from a cross-pollination conducted by the Inventor in Glandorf, Germany in November, 2011 of a unnamed selection of *Helleborus* x *ericsmithii*, not patented, as the female, or seed patent and an unnamed selection of *Helleborus* x *hybridus*, not patented, as the male, or pollen parent. The new *Helleborus* plant was discovered and selected by the Inventor as a single flowering plant from within the progeny of the stated cross-pollination grown in a controlled greenhouse environment in Glandorf, Germany in December, 2013.

Asexual reproduction of the new *Helleborus* plant by divisions in a controlled environment in Glandorf, Germany since March, 2014 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 5400'. These characteristics in combination distinguish 'COSEH 5400' as a new and distinct *Helleborus* plant:

1. Upright and mounded plant habit.
2. Moderately vigorous to vigorous growth habit.
3. Dark green-colored leaves.
4. Freely flowering habit.
5. Single white and red purple bi-colored flowers.
6. Good garden performance.

Plants of the new *Helleborus* differ from plants of the female parent selection in the following characteristics:

1. Plants of the new *Helleborus* are taller than plants of the female parent selection.
2. Plants of the new *Helleborus* have white and red purple bi- colored flowers whereas plants of the female parent selection have cream-colored flowers.

Plants of the new *Helleborus* differ from plants of the male parent selection in the following characteristics:

1. Plants of the new *Helleborus* have fewer leaves than plants of the male parent selection.

2. Plants of the new *Helleborus* have darker green-colored leaves than plants of the male parent selection.

Plants of the new *Helleborus* can be compared to plants of *Helleborus* x *ericsmithii* X *Helleborus* x *hybridus* 'COSEH 5100', disclosed in a U.S. Plant Patent application filed concurrently. Plants of the new *Helleborus* differ primarily from plants of 'COSEH 5100' in flower color as plants of the new *Helleborus* have white and red purple bi-colored flowers whereas plants of 'COSEH 5100' have light yellow green and red purple to greyed purple bi-colored flowers.

Plants of the new *Helleborus* can be compared to plants of *Helleborus* x *ericsmithii* X *Helleborus* x *hybridus* 'COSEH 5200', disclosed in a U.S. Plant Patent application filed concurrently. Plants of the new *Helleborus* differ primarily flower color as plants of the new *Helleborus* have white and red purple bi-colored flowers whereas plants of 'COSEH 5200' have purple-colored flowers.

Plants of the new *Helleborus* can be compared to plants of *Helleborus* x *ericsmithii* X *Helleborus* x *hybridus* 'COSEH 5300', disclosed in a U.S. Plant Patent application filed concurrently. Plants of the new *Helleborus* differ primarily from plants of 'COSEH 5300' in flower color as plants of the new *Helleborus* have white and red purple bi-colored flowers whereas plants of 'COSEH 5300' have purple-colored flowers.

Plants of the new *Helleborus* can also be compared to plants of *Helleborus* x *hybridus* 'Anna's Red', not patented. In side-by-side comparisons, plants of the new *Helleborus* differ primarily from plants of 'Anna's Red' in the following characteristics:

1. Leaves of plants of the new *Helleborus* have less distinct venation than leaves of plants of 'Anna's Red'.
2. Flowers of plants of the new *Helleborus* are white and red purple bi-colored whereas flowers of plants of 'Anna's Red' are red in color.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1 of 2) is a side perspective view of a typical flowering plant of 'COSEH 5400' grown in a container.

Figure 2:
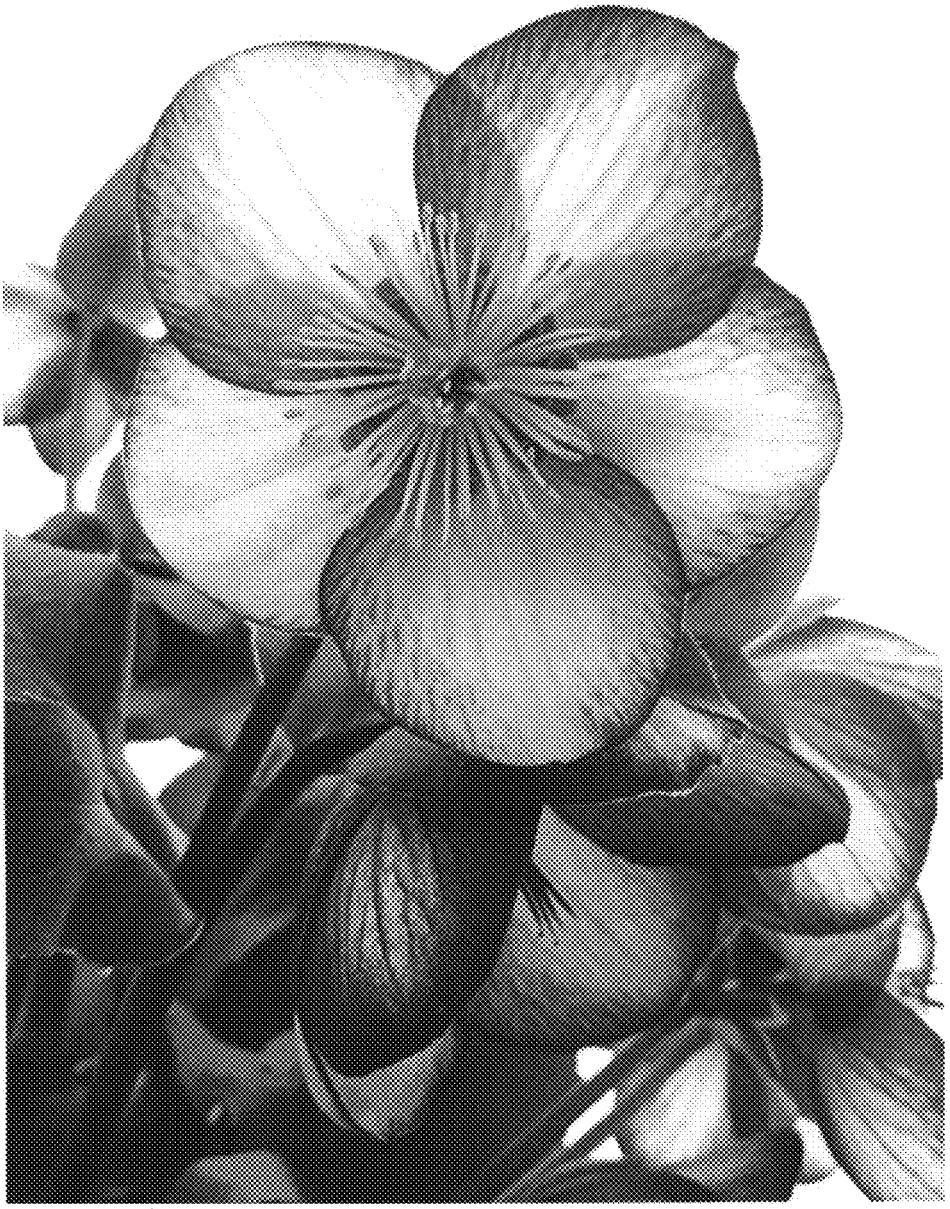

The photograph on the second sheet (FIG. 2 of 2) is a close-up view of typical flowers and leaves of 'COSEH 5400'.

DETAILED BOTANICAL DESCRIPTION

The aforementioned photographs and following observations, measurements and values describe plants grown during December in 17-cm containers in a glass-covered greenhouse in Glandorf, Germany and under cultural practices typical of commercial *Helleborus* production. During the production of the plants, day temperatures ranged from 12° C. to 32° C. and night temperatures ranged from 5° C. to 12° C. Plants were 14 months old when the photographs and the description were taken. In the following description, color references are made to The Royal Horticultural Society Colour Chart, 2015 Edition, except where general terms of ordinary dictionary significance are used.

Botanical classification: *Helleborus* x *ericsmithii* X *Helleborus* x *hybridus* 'COSEH 5400'.

Parentage:

*Female, or seed, parent*.—Unnamed selection of *Helleborus* x *ericsmithii*, not patented.

*Male, or pollen, parent*.—Unnamed selection of *Helleborus* x *hybridus*, not patented.

Propagation:

*Type*.—In vitro axillary meristem culture.

*Time to initiate roots, winter*.—About 55 days at temperatures about 12° C.

*Time to produce a rooted young plant, winter*.—About 170 days at temperatures ranging from 4° C. to 15° C.

*Root description*.—Thick to thin, fleshy; typically white to brown in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright and mounding plant habit with flowers held within and above the foliar plane; plant shape, roughly broadly ovate; moderately vigorous to vigorous growth habit and moderate to rapid growth rate.

*Plant height, soil level to top of foliar plane*.—About 29.3 cm.

*Plant height, soil level to top of flowers*.—About 46.8 cm.

*Plant diameter* (*area of spread*).—About 53.3 cm.

Leaf description:

*Arrangement*.—Leaves arranged in a basal rosette; leaves palmately compound with typically five leaflets per leaf.

*Leaf length*.—About 20.6 cm.

*Leaf width*.—About 21.8 cm.

*Leaflet length*.—About 12.9 cm.

*Leaflet width*.—About 7.6 cm.

*Leaf shape*.—Palmate; reniform in outline.

*Leaflet shape*.—Obovate to broadly elliptic.

*Leaflet apex*.—Acute.

*Leaflet base*.—Attenuate.

*Leaflet margin*.—Coarsely serrate; coarsely undulate.

*Leaflet texture and luster, upper and lower surfaces*.—Smooth, glabrous; leathery; slightly glossy.

*Leaflet venation pattern*.—Pinnate.

*Leaflet color*.—Developing leaflets, upper surface: Close to 143A; midvein tinged proximally, close to 178A. Developing leaflets, lower surface: Close to 146B; midvein tinged with close to 183B. Fully developed leaflets, upper surface: Slightly darker than NN137A; venation, close to 147B. Fully developed leaflets, lower surface: Close to 144B and towards the base, close to 183A; venation, close to 187A.

*Petioles*.—Length: About 18.8 cm. Diameter: About 7 mm to 8 mm. Strength: Strong. Texture and luster, upper and lower surfaces: Smooth, glabrous; moderately glossy. Color, upper and lower surfaces: Close to 145A; densely covered with fine dots, close to 183B.

Flower description:

*Flower shape and habit*.—Single rotate flowers; flowers slightly to moderately cupped; arranged solitary or in clusters with about nine flowers each; freely flowering habit with about 72 flowers developing per plant; flowers slightly nodding to facing outwardly.

*Fragrance*.—None detected.

*Natural flowering season*.—Plants begin flowering about ten months after planting; plants flower during the winter into the late winter in Germany.

*Flower longevity on the plant*.—About ten days; sepals persistent, other flower parts are not persistent.

*Flower buds*.—Length: About 1.9 cm. Diameter: About 1 cm. Shape: Ovate. Texture and luster: Smooth, glabrous; matte. Color: Close to 145D and distally, tinged with close to 64C to 64D.

*Inflorescence height*.—About 46.5 cm.

*Inflorescence diameter*.—About 20.1 cm.

*Flower diameter*.—About 7.3 cm by 7.3 cm.

*Flower depth* (*height*).—About 2.3 cm.

*Petals*.—All petals are transformed into nectaries.

*Sepals*.—Quantity and arrangement: About five, arranged in a single whorl. Length: About 3.8 cm. Width: About 3 cm. Shape: Broadly elliptic to broadly obovate, slightly to moderately concave. Apex: Obtuse to bluntly acute. Base: Truncate to broadly cuneate. Margin: Entire; slightly to moderately undulate. Texture and luster, upper surface: Smooth, glabrous; matte. Texture and luster, lower surface: Smooth, glabrous; slightly glossy. Color: When opening, upper surface: Close to 145D and distally, close to 145C; towards the margins and apex, close to 64D. When opening, lower surface: Close to 145C and distally, close to 145B; towards the margins and apex, close to 60D. Fully opened, upper surface: Close to 157A and distally, close to 145D; towards the margins and apex, close to 64B; venation, close to 64B; with development, colors becoming closer to 145D and towards the margins and apex, strongly tinged with close to 186C and outer edge, close to 64A. Fully opened, lower surface: Close to 157A and distally, close to 145D; towards the margins and apex, close to 64A; venation, close to 64A; with development, colors becoming closer to 157B, towards the margins, strongly tinged with close to 70B, towards the apex, close to between 71A and N186D and venation, close to 70A.

*Flower bracts*.—Quantity per flower: Typically one or two. Length: About 5.9 cm. Width: About 3.6 cm. Shape: Ovate to broadly ovate. Apex: Acute to emarginate. Base: Truncate. Margin: Distally, finely serrate and proximally, entire. Color, upper surface: Close to 137C; venation, close to 187B. Color, lower surface: Close to 147B; venation, close to 187B.

*Peduncles*.—Length: About 39.3 cm. Diameter: About 7 mm to 9 mm. Aspect: About 15° from vertical. Strength: Strong. Texture and luster: Smooth, glabrous; moderately glossy. Color: Close to between 145C and 150D; heavily and finely dotted, close to 183C.

*Pedicels*.—Length: About 1.5 cm. Diameter: About 2.5 mm. Aspect: About 25° from peduncle axis. Strength: Moderately strong. Texture and luster: Smooth, glabrous; glossy. Color: Close to 145C, finely dotted with close to 199B.

*Reproductive organs*.—Stamens: Quantity per flower: About 70. Filament length: About 1.1 cm. Filament color: Close to 157A. Anther shape: Double and broadly reniform; basifixed. Anther size: About 1 mm by 2 mm. Anther color: Close to 145C. Pollen amount: Scarce to moderate. Pollen color: Close to 4D to lighter than 4D. Pistils: Quantity per flower: About five, occasionally six or seven. Pistil length: About 1.4 cm. Stigma diameter: About 0.3 mm. Stigma shape: Club-shaped. Stigma color: Close to 157A. Style length: About 1.3 cm. Style color: Close to 186B. Ovary color: Close to between 145D and 150D. Nectaries (transformed petals): Quantity per flower: About 9 to 13. Length: About 1.1 cm. Diameter: About 2.5 mm. Shape: Tubular, slightly flattened. Texture and luster, inner and outer surfaces: Smooth, glabrous; slightly glossy. Color, immature, inner surface: Close to N144D. Color, immature, outer surface: Close to N144D; basal spot, close to 144A. Color, mature, inner surface: Close to N144A and distally, close to N144B; with development, close to N144C and distally, close to 151B to 151C. Color, mature, outer surface: Close to N144A and distally, close to N144B; basal spot, close to N148B; with development, close to N144C and distally, close to 151B to 151C; basal spot, close to 152C.

*Seeds and fruits*.—To date, seed and fruit development have not been observed on plants of the new *Helleborus*.

Garden performance: Plants of the new *Helleborus* have been observed to have good garden performance and to tolerate rain, wind, high temperatures about 35° C. and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'COSEH 5400' as illustrated and described.

* * * * *